Aug. 30, 1955 C. MALLERIN Plant Pat. 1,416
ROSE PLANT
Filed Nov. 10, 1954
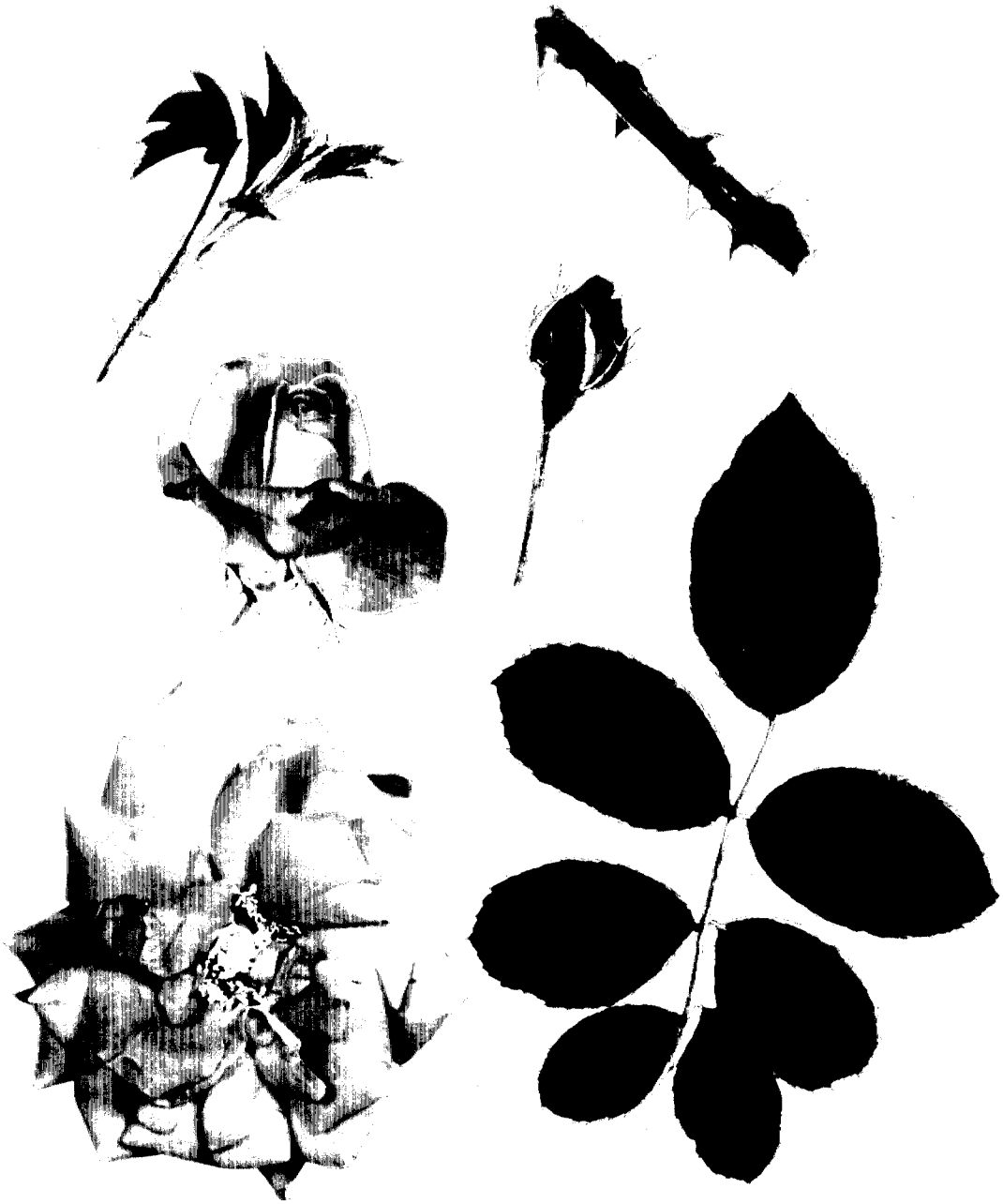
Inventor.
Charles Mallerin
By: Robb & Robb.
Attorneys.

United States Patent Office

Plant Pat. 1,416

Patented Aug. 30, 1955

1,416

ROSE PLANT

Charles Mallerin, Par le Pont-de-Claix, Isere, France, assignor to Jackson & Perkins Company, Newark, N. Y., a corporation of New York Application November 10, 1954, Serial No. 468,176

1 Claim. (Cl. 47—61)

The present invention relates to a new and distinct variety of rose plant of the climber class, which was originated by me by crossing "Paul's Scarlet Climber," unpatented, with an unnamed and unpatented multiflora seedling.

The primary objective of this cross was to produce a new variety of rose plant having the floriferousness characteristic of the seed parent, "Paul's Scarlet Climber," but which new variety bears flowers of a distinctively different color from anything heretofore known in commerce in the class of climbing roses. This objective was fully achieved, as evidenced by the fact that my new variety is very floriferous and bears flowers of a distinctive Scarlet Red general color tonality. In addition to these characteristics, the new variety is also endowed with desirable characteristics of repetition of bloom throughout the summer and fall, a shape and size of flower comparable to those of "Paul's Scarlet Climber," and very strong foliage which is Dark Cress Green in general color tonality and which is distinct from the color of any other climbing rose of which I am aware. These various characteristics, when considered together, constitute a unique combination, and distinguish my new variety from its parents, as well as from all other varieties.

Asexual reproduction of my new variety by budding at Newark, New York, and also at Pleasanton, California, U. S. A., shows that the foregoing characteristics and distinctions come true to form and are established and transmitted through succeeding propagations.

The accompanying drawing shows typical specimens of the foliage, stems and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Paul's Scarlet Climber."
- *Pollen parent.*—An unnamed multiflora seedling.

Classification:
- *Botanic.*—Climber.
- *Commercial.*—Climber.

FLOWER (Observations made from specimens grown in a field at Newark, New York, U. S. A., in the latter part of the month of August and in the early afternoon.)

Blooming habit: Recurrent—intermittent.

Bud:
- *Size.*—Medium.
- *Form.*—Ovoid; is not affected by wet or hot weather.
- *Color.*—When sepals first divide—Victoria Lake, Plate 1. When petals begin to unfurl—Eugenia Red, Plate 13. When half blown: Inside of petals—Spectrum Red, Plate 1, lightly overcast with Scarlet Red, Plate 1; reverse of petals—Pomegranate Purple, Plate 12, lightly overcast with Rose Red, Plate 12.

- *Sepals.*—Branched; curl back when petals begin to unfurl. Color: Inside—Pale Veronese Green, Plate 18; outside—Turtle Green, Plate 32.
- *Calyx.*—Color—Mineral Green, Plate 18. Shape—funnel. Size—small. Aspect—smooth. Odor when rubbed—none.
- *Peduncle.* — Length — medium. Aspect — rough. Color—Courge Green, Plate 17. Strength—erect; slender.
- *Opening.*—Opens up well; is not affected by adverse weather conditions.

Bloom:
- *Size.*—Medium; average size when fully expanded—3 inches.
- *Borne.*—Singly and several together.
- *Stems.*—Medium length; strong.
- *Form (when first open).*—Cupped. *Permanence*—retains its form to the end.
- *Petalage.*—Double (full but open center). Number of petals under normal conditions—from 30 to 35.
- *Color.*—Center of flower—Scarlet Red, Plate 1, lightly overcast with Scarlet, Plate 1. Outer petals—Scarlet Red, Plate 1, lightly overcast with Rose Doree, Plate 1. Base of petals (aiglet)—Citron Yellow, Plate 16. Inside of petals—Scarlet Red, Plate 1, lightly overcast with Scarlet, Plate 1. Reverse of petals—Spinel Red, Plate 26. General tonality from a distance—Scarlet Red, Plate 1.
- *Discoloration.*—General tonality at end of first day—Scarlet Red, Plate 1. Second day—Scarlet Red, Plate 1. Third day—Scarlet Red, Plate 1, lightly overcast with Scarlet, Plate 1.

Petals:
- *Texture.*—Leathery; is not affected by wet or hot weather.
- *Appearance.*—Inside—satiny. Outside—shiny.
- *Form.*—Oval; slightly notched.
- *Arrangement.* — Imbricated (regularly arranged shingle-like).
- *Petaloids in center.*—Few; small.
- *Persistence.*—Drop off cleanly.
- *Fragrance.*—Moderate. Nature—"Old Rose Perfume" (Centifolia).
- *Lasting quality.*—On the plant—long. As cut flower—long.

GENITAL ORGANS

Stamens, anthers: Medium size; many; regularly arranged around styles. Color—Yellow Ochre, Plate 15.

Stamens, filaments (threads)—medium length. Color—Alizarine Pink, Plate 13.

Pollen: Color—Warm Buff, Plate 15.

Styles: Columnar; uneven length; medium length; thin.

Stigmas: Color—Picric Yellow, Plate 4.

Ovaries: All enclosed in calyx.

Hips: None.

Seeds: None.

PLANT

Form: Climber.

Growth: Vigorous; branching.

Foliage: 5 to 7 leaflets.
- *Size.*—Medium and strong.
- *Quantity.*—Normal.
- *Color.*—New foliage: upper side—Yellowish Oil Green, Plate 5, overcast with Claret Brown, Plate 1; under side—Oxblood Red, Plate 1. Old foliage: upper side—Dark Cress Green, Plate 31; under side—Light Hellebore Green, Plate 17.

*Shape.*—Oval.
*Texture.*—Upper side—glossy. Under side—smooth.
*Ribs and veins.*—Light.
*Edge.*—Serrated (saw-toothed).
*Serration.*—Single; small.
*Leaf stem.*—Color—Absinthe Green, Plate 31. under side—prickles.
*Stipules.*—Medium length; smooth.

Wood:

*New wood.*—Color—Citron Green. Plate 31. Bark—smooth.
*Old wood.*—Color—Light Cress Green, Plate 31. Bark—smooth.

Thorns:

*Thorns.*—Quantity: on main stalks from base—ordinary; on laterals from stalk—ordinary. Form—narrow base; short; some straight and some hooked downward. Color (when young)—Acajou Red, Plate 13. Position—irregular.

*Prickles.*—Quantity: on main stalks—none; on laterals—none.
*Short needles.*—Quantity: on main stalks—none; on laterals—none.

I claim:

A new and distinct variety of rose plant of the climber class, substantially as herein shown and described, characterized particularly as to novelty by its floriferousness and repetition of bloom throughout the summer and fall, its very strong foliage and the distinctive Dark Cress Green general color tonality thereof, the shape and size of its flowers comparable to those of "Paul's Scarlet Climber" and the distinctive Scarlet Red general color tonality of its flowers.

No references cited.